US006268206B1

(12) United States Patent
Liptak

(10) Patent No.: US 6,268,206 B1
(45) Date of Patent: Jul. 31, 2001

(54) BIOREMEDIATION, DETOXICATION AND PLANT-GROWTH ENHANCING COMPOSITIONS AND METHODS OF MAKING AND USING SUCH COMPOSITIONS

(76) Inventor: David Liptak, 321 Kenwood Ave., Hamden, CT (US) 06518

( * ) Notice: Subject to any disclaimer, the term of this patent is extended or adjusted under 35 U.S.C. 154(b) by 0 days.

(21) Appl. No.: 09/417,571

(22) Filed: Oct. 14, 1999

Related U.S. Application Data

(60) Provisional application No. 60/107,290, filed on Nov. 6, 1998.

(51) Int. Cl.$^7$ .................................................. C12S 13/00
(52) U.S. Cl. ...................... 435/262.5; 435/244; 504/117
(58) Field of Search ............................ 435/262, 262.5, 435/244, 245, 252.2, 252.34, 174, 176, 177; 71/8–10; 504/117, 128, 196

(56) References Cited

U.S. PATENT DOCUMENTS

| | | | |
|---|---|---|---|
| 2,769,750 | 11/1956 | Harris | 195/116 |
| 2,919,194 | 12/1959 | Johnston | 99/96 |
| 3,224,946 | 12/1965 | Raymond | 195/116 |
| 3,261,761 | 7/1966 | Anderson | 195/96 |
| 3,871,957 | 3/1975 | Mohan et al. | 195/2 |
| 3,904,477 | * 9/1975 | Ishiyama . | |
| 4,088,659 | 5/1978 | Bhat et al. | 260/345 |
| 4,476,140 | 10/1984 | Sears et al. | 424/283 |
| 4,765,902 | 8/1988 | Ely et al. | 210/610 |
| 4,919,702 | 4/1990 | Weltzien et al. | 71/24 |
| 5,032,042 | 7/1991 | Schuring et al. | 405/258 |
| 5,133,625 | 7/1992 | Albergo et al. | 405/263 |
| 5,264,018 | 11/1993 | Koenigsberg et al. | 71/63 |
| 5,395,419 | 3/1995 | Farone et al. | 71/63 |
| 5,501,973 | 3/1996 | Mayfield | 435/244 |
| 5,560,737 | 10/1996 | Schuring et al. | 405/128 |
| 5,575,998 | 11/1996 | Nemec et al. | 424/93.3 |
| 5,653,675 | 8/1997 | Kanno et al. | 588/249 |
| 5,739,031 | * 4/1998 | Runyon . | |
| 5,770,436 | 6/1998 | Mayfield | 435/262.5 |
| 5,780,290 | 7/1998 | Rosenberg et al. | 435/243 |
| 5,843,427 | 12/1998 | Jones et al. | 424/93.4 |
| 5,854,059 | 12/1998 | Kozaki et al. | 435/262 |
| 5,863,789 | 1/1999 | Komatsu et al. | 435/262 |

FOREIGN PATENT DOCUMENTS 708672  12/1970  (ZA) .

OTHER PUBLICATIONS

Kodama. 'Microbial conversion of organic wastes to fuel. Microbial decomposition of articial aromatic compounds.' Denryoku Chuo Kenkyusho Hokoku (1979), 477007.*
*Cyclic Amp in Prokaryotes*, H.V. Rickenberg, National Jewish Hospital and Research Center and Department of Biophysics and Genetics, University of Colorado School of Medicine, Denver, Co. 1974, pp. 353–369.

*Degradation of Organochlorine Pesticides, Particularly Endosulfan, By Trichoderma Harzianum*, A. Katayama, F. Matsumura, Environmental Toxicology and Chemistry, vol. 12., 1993, pp. 1059–1065.

*The Metabolic Code*, G.M. Tomkins, Science vol. 189, Sep. 5, 1975 pp. 760–763.

*Biodegradation and Bioremediation*, M. Alexander, Academic Press, copyright 1994, pp. 36–49.

*Bioremediation*, K.H. Baker, D.S. Herson, McGraw–Hill, pp. 18–19 & 112–113, 150–151, 156–157 and 228–229, (1994).

*Microbial Biotransformation of Carbon–13 Isotope Labeled Benzene in Soil*, D.J. Liptak, Master of Forest Science Research Project, Yale University, May 9, 1995, pp. 1–22.

*The Use of Organic Biostimulants to Reduce Fertilizer Use, Increase Stress Resistance, and Promote Growth*, G.P. Berlyn, S. Sivaramakrishnan, 1996, National Proceedings, Forest and Conservation Nursery Associations. Gen. Tech. Rep. PNW–GTR–389, 1996, pp. 106–112.

Abstract: *Enhanced Instrinsic Bioremediation of Hydrocarbons Using an Oxygen–Releasing Compound*, Journal of Remediation, Autumn 1996, No. 4.

Homepage Jul. 6, 1999, *Regenesis*, http://www.regenesis.com/ Jul. 6, 1999, p. 1 pp. 1–2.

*Regenesis Oxygen Release Compound, ORC*, http://www.regenesis.com/orchome.htm, Jul. 6, 1999, p. 1.

*Field Applications of In Situ Remediation Technologies: Chemical Oxidation*, http://www.clu–in.org/PRODUCTS/MOREINFOR/Ischemox.htm p. 1, Jul. 6, 1999.

*Terra–Clean, Enhanced In–Situ Remediation Technology*, http://www.terraliftinternational.com/Clean2.html pp. 1–2, Jul. 6, 1999.

*Pollution Online, Hydraulic and Pneumatic Fracturing Fosters Soil Remediation*, http://news.pollutioonline.com/feature–articles/1997 1126–34.html, Nov. 26, 1997 pp. 1–3.

*Identification and role of adenylyl cyclase in auxin signaling in higher plants*, T. Ichikawa, Nature, vol. 390(6661), 12/97, pp 698–701.

*Plant cyclic AMP comes in from the cold*. A. Trewavas, Nature, vol. 390(6661), 12/97, pp657–658.

* cited by examiner

Primary Examiner—William H. Beisner
(74) *Attorney, Agent, or Firm*—St. Onge Steward Johnston & Reens, LLC

(57) ABSTRACT

A composition containing cAMP, cGMP, forskolin, adenylate cyclase or guanylate cyclase and microorganisms is provided to facilitate bioremediation, detoxication and to enhance plant growth in media contaminated with petroleum hydrocarbons. Methods to make the composition and apply it to the contaminated media in order to facilitate bioremediation and detoxication of such contaminants are also provided.

22 Claims, No Drawings

BIOREMEDIATION, DETOXICATION AND PLANT-GROWTH ENHANCING COMPOSITIONS AND METHODS OF MAKING AND USING SUCH COMPOSITIONS

PRIOR APPLICATION

This application claims the benefit of U.S. Provisional Application Ser. No. 60/107,290 filed Nov. 6, 1998.

FIELD OF THE INVENTION

The invention relates to compositions for bioremediation and detoxication of contaminated media and facilitating plant growth in contaminated media. More specifically, compositions containing microorganisms treated with compounds containing any one of: cyclic adenosine monophosphate (cAMP), cyclic guanosine monophosphate (cGMP), adenylate cyclase, guanylate cyclase, forskolin, or the homologs, analogs and derivatives of such compounds, and methods for making and using such compositions are disclosed.

BACKGROUND OF THE INVENTION

Hydrocarbons, including petroleum based hydrocarbons, can be released into the environment from industrial processes through discharges and emissions, from surface spills such as open water spills, above ground storage tank overfilling and releases, from oil spills and tanker purging during ship transport, from oil drilling and exploration operations, from agricultural operations such as cropland weed and pest management associated with chemical applications, and from subsurface releases such as leaking underground storage tanks, undesirably polluting the environment. "Petroleum based hydrocarbons" is understood to include by way of example, and not as a limitation to the present invention, chemicals toxic to the environment such as crude oil, distilled or refined fuels, halogenated pesticides, halogenated herbicides, halogenated aromatic hydrocarbons, polycyclic aromatic hydrocarbons, and/or methane and the like. Release of such toxic chemicals is referred to herein as a "contaminant". The environment into which the contaminant is released, be it liquid or solid or gaseous media, includes by way of example, and not as a limitation to the present invention, surface water, ground water, wells, rivers, estuaries, the ocean, surface sediment, subsurface soil, surface soil, foliage and/or soil containing natural plant growth, and/or air, and the like and is referred to herein as "contaminated media".

Oil spilled at sea often reaches the littoral zone and becomes coated on or mixed with soil, or other solids, such as rocks, and vegetation. Oil adsorption and absorption on or in these materials renders the petroleum contaminants less mobile and difficult to clean up or remediate using conventional physical/mechanical remediation techniques, such as filtering, excavation or mechanical removal. Such techniques also tend to adversely affect the ecosystems in proximity to the contaminants.

Contaminants discharged from industrial processes are often mixed as an aqueous influent to treatment systems and then as an effluent to receiving waters. These chemicals are also adsorbed on suspended solids in water and can settle out and thus become incorporated into the sediment. Once settled in the sediment, the contaminants become less mobile and difficult to remediate using conventional physical/mechanical remediation techniques without causing damage to surrounding ecosystems.

Herbicides and pesticides used in cropland management are applied to plants and released in spills or as excess in over application. These applications and releases are washed into the soil and plants from irrigation practices or from atmospheric precipitation. Such herbicides and pesticides accumulate in the rhizosphere where conventional physical/mechanical remediation techniques also prove difficult or detrimental to the surrounding ecosystem.

Distilled or refined fuels, including chemical mixtures such as gasoline and diesel fuels stored in above ground or underground storage tanks released to the environment from overspills during tank filling and tank and piping failures are adsorbed or absorbed respectively into the soil and plants adjacent to such releases. There they tend to become less mobile and/or accumulate on or in the groundwater resulting in dissolved aqueous and non-aqueous phase liquids containing these chemical contaminants. Further migration of these chemicals also results in widespread aquifer contamination. Such contaminated media are also difficult to remediate and can harm human health and sensitive ecosystems.

Bioremediation of these contaminants tends to be the best technology and most cost effective means to remediate such contaminated media. What is meant by "bioremediation" or "bioremediation activity" is the microbial oxidation and/or mineralization (i.e., biodegradation) of contaminants. "Mineralization" means the bioconversion of contaminants to carbon dioxide, water and occasionally new microbial cell growth. "Detoxication" (sometimes designated "detoxification") refers to the change in a contaminant (molecule or complex mixture) that renders it less harmful to one or more susceptible organisms (i.e. microorganisms, plants, animals or humans). See M. Alexander, *Biodegradation and Bioremediation*, pp. 41–48 (1994), incorporated herein by reference.

Many naturally occurring microorganisms are useful in microbial oxidation and mineralization of such contaminants because they generate enzymes that oxidize and mineralize the contaminants through what is known metabolically as catabolism. However a disadvantage of conventional microbial oxidation and mineralization is that the rate of biochemical oxidation (i.e., bioremediation) of the contaminated media is often undesirably slow. One reason for the slow bioremediation rate of the contaminants is that the microbes may exist only in small amounts naturally in the contaminated media. It has also been purported that useful indigenous microorganisms tend to be attacked by predatory microorganisms, thereby keeping the amount of indigenous microorganisms relatively low. In addition, naturally occurring microorganisms may only produce small amounts of the enzymes required for oxidation and mineralization thereby also causing slow oxidation and mineralization rates of the contaminants. It is believed that the rate of enzyme production occurs at low rates and can be ultimately inhibited through a cellular phenomenon known as catabolite repression.

It is known that microorganisms tend to exhibit decreased production of enzymes useful in oxidizing and mineralizing contaminants when insulted with toxic contaminants thereby decreasing or stopping the rate of biodegradation of such contaminants. These reasons, either combined or independently, render microbial biodegradation of contaminated media undesirably slow and/or incomplete to mineralization.

Genetically engineered microorganisms (GEMs) have been developed in an attempt to overcome some of the above problems with naturally occurring microorganisms. GEMs however tend to be unacceptable to environmental regulatory authorities for widespread and uncontrolled environmental application due to their uncertain effects on the environment.

There are numerous enzymes present in microorganisms known to catalyze the biodegradation of the contaminants. In bacteria, cAMP has been found to play a role in the formation of the constitutive enzymes necessary to catalyze the breakdown of secondary sugars such as galactose and arabinose in the presence of glucose. However, enzymes known to be associated with the break down of sugars, such as glucose, lactose and galactose, and not those associated with the oxidation and mineralization of toxic contaminants tend to exhibit cAMP induced activity. For example, H. V. Rickenberg, *Cyclic AMP in Prokaryotes*, pp. 353–369 (1974), ("Rickenberg"), describes the synthesis of several proteins (enzymes) controlled by cAMP. It has been demonstrated that cAMP is required for the effective synthesis of beta-galactosidase and tryptophanase in *E. Coli*. Rickenberg further describes that in "*E. Coli* exogenous cAMP overcomes both the severe transient (citation omitted) and less severe steady-state catabolite repression (citation omitted) of the synthesis of beta-galactosidase caused by the presence of glucose in the medium." H. V. Rickenberg, *Cyclic AMP in Prokaryotes*, pp. 354–355.

It was found that inhibition of biolumenescence of Photobacterium phosphoreum is a useful measure of general toxicity associated with solids including soil. K. K., Kwan, *Direct Solid Phase Toxicity Testing Procedure*, 8 Environ. Toxicol. Water Qual., 345, (1993), incorporated herein by reference. The MICROTOX® solid phase test kit is based on the inhibition of the biolumenescence enzyme system associated with the test marine bacterium (*Photobacterium phospherum*). See also M. W. Greene, et al., *Measurement of Soil and Sediment Toxicity to Bioluminescent Bacteria When In Direct Contact for a Fixed Time Period*, 53–63, Proc. 65$^{th}$ Annu. Conf. & Expos., New Orleans, La., Sep. 20–24, 1992; K. K. Tung, et. al., *The Solid Phase Assay: New Microtox Test Procedure*, Proc. 17$^{th}$ Annu. Aquatic Toxicity Workshop, November 5–7, Vancouver B.C., Vol. 1, 1991.

Moreover, it is known from soil ecotoxicology that the de novo biosynthesis of beta-galactosidase induction is inhibited by the presence of a toxic xenobiotic and has been correlated to a decrease in biomass production in plants. Toxicity tests in soil have been based on such enzyme inhibition phenomena. For example, the direct solid phase toxicity testing procedure which uses the Toxi-Chromotest kit is based on inhibition by chemicals of the de novo biosynthesis of beta-galactosidase. K. K., Kwan, *Direct Toxicity Assessment of Solid Phase Samples Using the Toxi-Chromotest Kit*, 8 Environ. Toxicol. Water Qual., 223, (1993). Therefore it is known that the presence of toxic xenobiotics in soil tends to inhibit certain enzyme activity responsible for biodegradation.

According to M. Alexander, *Biodegradation and Bioremediation*, pp. 36–40, (1994), ("Alexander"), incorporated herein by reference, constitutive enzymes are produced by certain microorganisms regardless of whether substrates for those enzymes are present. By contrast, inducible enzymes are only formed in appreciable amounts when the substrate, or a structurally related compound, is present. Induction is known to be a complex process and involves particular substrates which induce or increase the rate of formation of certain degradative enzymes. However, because xenobiotics, more particularly, petroleum based hydrocarbons, are known to inhibit certain enzyme activity responsible for biodegradation, constitutive enzymes known to catalyze the breakdown of sugars such as glucose, lactose and arabinose are often ineffective for bioremediating contaminants which are structurally different than sugars, and which also require inducible enzymes for their degradation.

In addition, the products of catabolism (catabolites) can act as repressors inhibiting the formation of inducible enzymes. This inhibition is known as "catabolite repression" and according to Alexander, controls the enzymatic population where products generated during catabolism of one substrate can repress the synthesis of enzymes that function to degrade a second substrate. Catabolite repression has been implicated in diauxie growth and usually occurs where a preferred energy source, such as carbon from sugar is present and catalyzed first which accordingly represses catabolic inducible enzymes required for the biodegradation of complex contaminants.

Recent research indicates that cAMP may also play a role concerning signal transduction with the plant hormone auxin. See Ichikawa, et al., *Identification and Role of the Known Adenyl Cyclase In Auxin Signaling and Higher Plants*, Nature, Vol. 390 (6661), December 18/25 (1997) pp. 689–701 ("Ichikawa"). Ichikawa discloses findings relating to tobacco protoplasts expressing the enzyme adenylyl cyclase which produces cAMP. Ichikawa discloses that the cAMP generated by the tagged tobacco protoplasts can replace auxin in triggering its cell division, and suggests that cAMP may be part of the auxin signal-transduction pathway. However, it is also known that there are toxic effects associated with high levels of auxin and that many herbicides are synthetic auxins which can inhibit the growth of plants. See U.S. Pat. No. 4,919,702 to Weltzien et al., hereby incorporated by reference. A chemical is considered "phytotoxic" when its presence reduces the growth or alters normal development of plants. Thousands of organic chemicals termed "phytotoxins" have such properties.

Forskolin, also called colforskoli, a diterpene, induces cAMP formation. Forskolin binds to the catalytic site of adenylate cyclase which is the enzyme responsible for the formation of cAMP in the microbial cell. At the concentration of about 10 micromole/liter, forskolin causes an increase in the cellular concentration of cAMP by activating adenylate cyclase. Yet forskolin is also known to be useful in the treatment of glaucoma. U.S. Pat. No. 4,476,140 to Yale University describes the use of forskolin in the treatment of glaucoma in mammals, hereby incorporated by reference. Forskolin, as does cAMP, possesses vasodilating and cardiostimulating properties, apparently due to its basic ability to stimulate the adenylate cyclase and thus increase the cellular concentration of cAMP in mammals. See U.S. Pat. Nos. 4,088,659, and 4,476,140, hereby incorporated by reference.

A disadvantage to the prior art of remediating pollutants contained in contaminated media is that often the nature of the media, and the extent of its contamination requires the application of bioremediation techniques in order to prevent concomitant damage to the surrounding ecosystems. The dilemma has been that the very nature of such toxic contaminants, like petroleum based hydrocarbons, inhibit enzymatic induced catabolism known to be responsible for metabolic degradation of xenobiotics. Moreover, enzymes known to be effective for the degradation of simple sugars, or believed to be linked to the regulation of certain plant cell division have not been shown to be useful or effective in oxidizing and mineralizing xenobiotic contaminants, detoxifying contaminated media or promoting the growth of such plants in the presence of such contaminants.

What is desired, therefore, is a composition comprising a mixture of microorganisms and compounds which result in the rapid oxidation, detoxification, and mineralization of contaminants that can be applied to contaminated media that have been previously difficult to remediate using conventional techniques. What is further desired is a mixture of microorganisms and compounds, wherein the mixture results in a more rapid oxidation and mineralization of contaminants by the microorganisms than without the compounds, thereby facilitating bioremediation and detoxication of contaminated media and also resulting in enhanced plant growth in such contaminated media, and methods for making and using such compositions.

SUMMARY OF THE INVENTION

Accordingly, it is an object of the invention to provide a composition comprising a mixture of microorganisms and compounds of cAMP, cGMP, and/or forskolin, or homologs, analogs and derivatives thereof having bioremediating activity to facilitate bioremediation and/or detoxication of contaminated media.

Another object of the present invention is to provide a composition comprising a mixture of microorganisms and compounds containing adenylate cyclase, guanylate cyclase, and/or forskolin or homologs, analogs and derivatives thereof having bioremediating activity to facilitate bioremediation and/or detoxication of contaminated media.

A further object of the invention is to provide a method of making a mixture of microorganisms and compounds of cAMP, cGMP, adenylate cyclase, guanylate cyclase, and/or forskolin, or homologs, analogs and derivatives thereof having bioremediating activity to facilitate bioremediation and/or detoxication of contaminated media.

Yet another object of the present invention is to provide a method of using a mixture of microorganisms and compounds containing cAMP, cGMP adenylate cyclase, guanylate cyclase, or forskolin, or homologs, analogs and derivatives thereof having bioremediating activity to facilitate bioremediation and/or detoxication of contaminated media.

A further object of the invention is to provide a composition comprising a mixture of microorganisms and compounds of cAMP, cGMP, adenylate cyclase, guanylate cyclase, and/or forskolin, or homologs, analogs and derivatives thereof to facilitate plant growth in contaminated media.

To overcome the deficiency of the prior art and to achieve at least some of the objects and advantages listed above, the present invention provides: a composition to facilitate bioremediation and detoxication of contaminants in contaminated media, a composition to facilitate the growth of plants grown in contaminated media, a method to make a composition to facilitate bioremediation and detoxication of contaminants in contaminated media and a method to facilitate bioremediation and detoxication of contaminants in contaminated media.

The composition to facilitate bioremediation and detoxication of contaminants in contaminated media according to the present invention comprises: a mixture of at least one compound selected from the group consisting of cAMP, cGMP, forskolin, adenylate cyclase and guanylate cyclase or derivatives, homologs, or analogs thereof and at least one microorganism specie, wherein the mixture is effective to facilitate bioremediation and detoxication of the contaminants in the contaminated media.

The composition to facilitate the growth of plants grown in contaminated media according to the present invention comprises: a mixture of at least one compound selected from the group consisting of cAMP, cGMP, forskolin, adenylate cyclase and guanylate cyclase, or derivatives, homologs, or analogs thereof and at least one microorganism specie, wherein the mixture is effective to facilitate the growth of plants grown in contaminated media.

The method to make a composition to facilitate bioremediation of contaminants in contaminated media comprises the steps of: providing at least one compound selected from the group consisting of cAMP, cGMP, forskolin, adenylate cyclase and guanylate cyclase, or derivatives, homologs, or analogs thereof in a solution to form an aqueous phase and adding at least one miroorganism specie to the aqueous phase to form a mixture, wherein the mixture is effective to facilitate bioremediation of the contaminants.

The method to facilitate bioremediating contaminants in contaminated media according to the present invention comprises the steps of: mixing at least one compound selected from the group consisting of cAMP, cGMP, forskolin, adenylate cyclase and guanylate cyclase or derivatives, homologs, or analogs thereof and at least one microorganism specie to form a mixture; and applying said mixture to the contaminated media in an amount effective to facilitate bioremediation of the contaminants.

The invention and particular features will become more apparent from the following detailed description considered with reference to the accompanying examples.

DETAILED DESCRIPTION OF THE INVENTION

Novel compositions comprising a mixture of microorganisms and molecules of cAMP, cGMP, adenylate cyclase, guanylate cyclase, and/or forskolin, or homologs, analogs and derivatives thereof having bioremediation activity to facilitate bioremediation of contaminants in contaminated media are described. An associated method of making, using, and applying the compositions are also provided. What is meant by the term "a composition effective to facilitate bioremediation" is a composition which increases the rate of biodegradation of contaminated media than without its addition or biodegradation of contaminants that would not be biodegraded or would proceed at a slower rate without the composition. Microorganisms suitable for use in the inventive compositions include naturally occurring, indigenous, genetically engineered or added microorganisms capable of metabolizing contaminants in contaminated media. Preferably, microorganisms effective in degrading and mineralizing petroleum based hydrocarbons are used. More preferably, these microorganisms include the following bacteria and fungi: *Phanerochate chrysosporium; Pseudomonas sp.; Micrococcus sp.; Arthrobacter sp.; Candida sp.; Phanerochate sp.* (i.e., white rot fungus) and *Trichoderma sp.*

Microorganisms useful for the present invention may also be those microorganisms indigenous in soil, water or air. Such microorganisms known to those skilled in the art may also be available from the American Type Culture Collection (ATCC). Specifically identified as useful are the following microorganisms listed in Table 1.

TABLE 1

| MICROORGANISM | REFERENCE |
|---|---|
| *Pseudomonas putida*, ATCC No. 49451 | Applied. Microbiol. Biotech., 30: 426– |
| Degradation of phenol in mixed culture. | 432, 1989 |
| *Pseudomonas fluorescens*, | Applied Environ. Microbiol., 50: |

TABLE 1-continued

| MICROORGANISM | REFERENCE |
|---|---|
| Utilizes p-cresol as sole carbon source. Degradation of phenol. | 946–950, 1985 |
| Pseudomonas Sp., *Micrococcus dentrificans*, ATCC No. 21909 Exxon Res. and Eng. Co. M-30-m, Oil contaminated beach sample, dispersion and degradation of oil. | U.S. Pat. No. 3,871,957 |
| *Alcaligenes eatrophus*, (*Hydrogenomonas eutropha*) ATCC No. 17697 Dissimilation of aromatic compounds. and regulation of B-ketoadipate pathway. | J. Bacteriology, 107: 468-475 and 476–485, 1971; Arch. Milcrobiol., 70: 2, 1970. |
| *Mycobacterium aurum*, (*Mycobacterium cuneatum*) ATCC No. 21498 Nippon Oil Co., Ltd. Cutting material from an oil well. Production of single cell protein utilizing hydrocarbons and n-paraffins. | U.S. Pat. No. 3,888,736 |
| *Mycobacterium fortuitum*, (*Mycobactedum tuberculosis*) ATCC No. 15073 Sun Oil Co. Utilization of hydrocarbons in the production of amino acids. | U.S. Pat. No. 3,219,543 |
| *Mycobacterium paraffinicum*, ATCC No. 12670 Magnolia Petroleum Co. Soil, Easton, LA. Utilizes ethane or hydrocarbons higher than ethane in paraffin series as a sole source. | App. Microbiol., 4: 310–315, 1956 |
| *Mycobacterium petroleophilum*, ATCC No. 21497 Nippon Oil Co., Ltd. Core sample from a drilling well. Production of single-cell protein utilizing hydrocarbons and n-paraffins. | U.S. Pat. No. 3,888,736 |
| *Mycobacterium phlei*, ATCC NO. 15610 Commercial Solvents Corp., Kerosene storage container. Production of organic, nitrogenous materials with aliphatic hydrocarbons as energy source. | U.S. Pat. No. 3,627,637 |
| Mycobactedum Sp. (*Mycobacterium album*) ATCC No. 29676 J. J. Perry Soil. Metabolism of propane, n-propylamine and propionate. | J. Bacteriol., 112: 513–518, 1972; Degradation of cycloparaffinic hydrocarbons, J. Gen. Microbiology., 82: 163–169, 1974 |
| *Pseudomonas aeruginosa*, ATCC No. 21472 Soil from an oil field. | U.S. Pat. No. 3,729,378 |
| *Pseudomonas aeruginosa* ATCC No. 33988 Fuel storage tank, Ponca City, OK. Testing of anti microbial agents in distiliate fuels. | ASTM E1259-88 |
| *Pseudomonas alkanolytica* ATCC No. 21034 *Pseudomonas aromatica* ATCC No. 23315 | U.S. Pat. No. 3,669,836 |
| *Aspergillus flavus*, ATCC No. 26873 | Dr. Frank I. Reiff 19: 429, Degradation of n-alkanes, Naturwissenschaflen, 59: 1–2, 1972 |
| *Trichoderma Harzianum*, ATCC No. 2023 Rodococcus sp., ATCC Nos. 21504, 21507, 21508 Achromobacter sp., ATCC No. 21910 Acinetobacter sp., ATCC No. 31012 Arthrobacter sp., ATCC No. 21908 | U.S. Pat. Nos. 3,769,164; 3,769,164; 3,769,164, respectively U.S. Pat. No. 3,871,957 |
| SS *Nocardia paraffinae*, ATCC No. 21509 | U.S. Pat. No. 3,871,957 |
| *Phodococcus globerus*, | U.S. Pat. Nos. 3,769,164; |
| ATCC Nos. 21505, 21506 Pseudomonas sp., ATCC No. 21909 | 3,769,164, respectively U.S. Pat. No. 3,871,957 |

The above references are incorporated herein by reference in their entireties. In addition to his relatively short list are those agents cited or otherwise referred to in the references identified by this application, all of which are incorporated herein by reference. Additionally, other microorganisms useful in the inventive compositions may also be discovered, produced or grown in accordance with the skill in the art, whether now known or which will be later developed, including microorganisms produced using recombinant DNA technology. For example, microorganisms or plants may be developed using recombinant DNA techniques for producing the enzyme adenylate cyclase, guanylate cyclase, and/or forskolin. Microorganisms or plants altered to produce such compounds can create an increase in concentration of molecules of cAMP, cGMP, and/or forskolin, or homologs, analogs and derivatives thereof useful to make the inventive compositions, in addition to those microorganisms or plants that actually function to mineralize and oxidize the contaminants. Naturally occuring microorganisms, plants or GEMs having such genetic information can be useful to make the inventive compositions and methods.

In addition, it is known that the enzyme phosphodiesterase hydrolyzes cAMP and cGMP and therefore compounds which inhibit phosphodiesterase, such as theophylline, can ultimately regulate the concentration of cAMP and cGMP. It is also known that phosphodiesterase can be produced in bacteria, such as *E. Coli*, and that mutant strains defective in phosphodiesterase can be isolated. Therefore, microorganisms that have been genetically altered to under express phosphodiesterase can also prove useful in the inventive compositions and methods.

Molecules of cAMP, cGMP, adenylate cyclase, guanylate cyclase, forskolin, or the homologs, analogs and derivatives of such compounds that show bioremediation activity when mixed with microorganisms and applied to contaminated media are useful compounds to make the inventive compositions. Such synthetic or natural derivatives of cAMP, cGMP, and/or forskolin are also useful compounds to make the inventive compositions. Derivatives of cAMP, cGMP, and forskolin that are less polar are preferred, and dibutyryl cAMP, cGMP, and forskolin are most preferable. Derivatives of cAMP, cGMP or forskolin may be synthesized, or isolated from mammalian or plant sources using methods known to those skilled in the art. For example, forskolin may be isolated from the plant *Coleus forskohlii*, as provided in U.S. Pat. No. 4,088,659 which is hereby incorporated by reference. The cAMP, cGMP, and forskolin derivative compounds are also available commercially from chemical suppliers such as Sigma, Aldrich, and Merck.

In one aspect, the inventive composition can be formed where at least one specie of microorganisms is mixed in a solution of at least one derivative of cAMP, cGMP, and/or forskolin at standard conditions to form a mixture. The solution is preferably pH-adjusted. Preferably, a $1 \times 10^{-5}$ Molar solution of at least one derivative of any of cAMP, cGMP or forskolin is used. By way of example and not as a limitation to the present invention, derivative compounds of cAMP suitable for use in this invention include the sodium salts of $N^6$-monoacetyladenosine 3':5'-cyclic monophosphate, $N^6$-monobutyryladenosine 3':5'-cyclic monophosphate, $N^6$-monooctanoyladenosine 3':5'-cyclic monophosphate, 2'-O-monobutyryladenosine 3':5'-cyclic monophosphate, $N^6$-2'-O-diacetyladenosine 3':5'-cyclic monophosphate, and $N^6$,2'-O-dibutyryladenosine 3':5'-cyclic monophosphate (i.e., dibutyryl cAMP). Similarly, by way of example and not as a limitation to the present invention, derivative compounds of forskolin suitable for use in this invention include dibutyryl forskolin and diterpene forskolin.

Preferably between about 2 mg/liter of an aqueous solution of cAMP, cGMP or forskolin derivatives are used with about 1,000,000 to about 5,000,000 count of microorganisms. Most preferably, about 2 mg/liter of an aqueous solution of a cAMP derivative is used for about every 2,000,000 count of microorganisms. Hereinafter, these microorganisms will be referred to as "treated microorganisms".

This mixture may be further processed by mixing inert adsorbents with the treated microorganisms. This is preferable when using treated microorganism compositions in freeze dried form for bioremediating contaminated media comprising contaminants on surface waters. It is believed the inert adsorbents facilitate the immobilization of the contaminant on surface waters. In addition, inert adsorbents further assist in immobilizing the microorganisms to help prevent their biodegradation or expiration during storage. Inert adsorbents useful in the present invention by way of example and not as a limitation of the present invention include kaolin, vermiculite, perlite, clay, glass beads or zeolites. For example, U.S. Pat. No. 3,224,946 discloses a method for immobilizing microorganisms using natural zeolites in microbial conversion of hydrocarbons, and U.S. Pat. No. 2,769,750 discloses a process involving the action of microorganisms on organic substances using inert adsorbents. U.S. Pat. No. 3,224,946 and U.S. Pat. No. 2,769,750 are incorporated herein by reference. Preferably, between about 1 gram of kaolin, vermiculite, perlite, clay or glass beads are used for about 1,000,000 to about 5,000,000 count of microorganisms contained in one liter of solution.

Nutrients are preferably added to the treated microorganisms or the treated microorganisms with inert adsorbents when bioremediating contaminated media containing plants. Preferably, between about 1 gram of 15-30-15 nitro-gen-phoshorous-potassium fertilizer is used for one liter of solution containing about 5,000,000 count of microorganisms. Even more preferably, for petroleum contamination, a lipophillic form of fertilizer may be used.

The treated microorganisms are preferably freeze dried to form an anhy- drous powder using methods known to those skilled in the art. For example, U.S. Pat. Nos. 3,261,761 and 2,919,194 disclose methods for freeze drying, and drying by evaporation, and are incorporated herein by reference.

The reconstituted mixture containing treated microorganisms, inert adsorbents and/or nutrients may be applied directly to contaminated media by spraying on, pouring into, admixing with, or injection into the contaminated media, using methods known to those skilled in the art. For example, when using a solution of the anhydrous powder with inert adsorbents, methods for applying the inventive compositions to open seas or littoral zones are provided in U.S. Pat. No. 3,871,957, and South African Patent Document Serial No. 708,672, incorporated herein by reference. Effective amounts of the inventive compositions for application to open seas and littoral zones are preferably applied by pouring or spraying, and can be determined by first testing about three representative 10 meter by 10 meter areas. Effective amounts are then calculated based on the observed rates of biodegradation determined from chemical analysis known in the art. Effective amounts of the inventive compositions for application to subsurface soils, preferably by injection, are calculated by multiplying the estimated mass and/or volume of contaminants by scale-up factors determined by pilot testing in the field and methods known in the art.

What is meant by "effective amounts to facilitate bioremediation" or "an amount effective to facilitate bioremediation" is an amount of the composition applied to the contaminated media which increases the rate of biodegradation of contaminated media than without its addition or biodegradation of contaminants that would not be biodegraded or would proceed at a slower rate without the applied composition. What is meant by "effective amounts to facilitate detoxication" or "an amount effective to facilitate detoxication" is an amount of the composition applied to the contaminated media which increases detoxication of contaminated media than without its addition or detoxication of contaminants that would not be changed or change at a slower rate without the applied composition. For certain subsurface applications, by way of example and not as a limitation to the present invention, such as in aquifer and soil contaminations, dissolved oxygen concentration of the mixture can be elevated above lower levels (i.e. less than 1–2 mg/liter) encountered in the contaminated media by use of high-pressure (i.e., greater than 1 atmosphere) gaseous oxygen in the form of high purity oxygen or enriched air, or chemically bound oxygen in a second compound, such as in the form of magnesium peroxide ($MgO_2$) oxygen release compound ORC®). See U.S. Pat. Nos. 5,264,081 and 5,395,419, incorporated herein by reference. The oxygen may be injected in stoichiometric amounts to oxidize the estimated contaminant concentration and support the oxygen uptake of the microorganisms with adjustments by scale-up factors determined by pilot testing in the field with effective amounts of the inventive compositions. In this process a mixture of the composition, water and air with or without gaseous oxygen is injected into the contaminated zones in the subsurface environment using known subsurface drilling, hydrofracturing and injection techniques such as provided in U.S. Pat. Nos. 5,560,737 and 5,032,042, incorporated herein by reference, by way of example and not as limitation to the present invention, or other methods in accordance with the skill in the art, whether now known or later developed.

If a freeze dried mixture of treated microorganisms is used, then it is preferably mixed with an aqueous phase to form a suspension or slurry. Preferably, between about 1 liter of a solution of an aqueous phase is used for about 1 gram of the freeze dried mixture. "Aqueous phase" means any liquid phase containing water, including fresh water, seawater, USP distilled water, or fresh water or seawater with organic and/or inorganic nutrients.

The treated microorganisms may oxidize and mineralize contaminated media faster and to a greater efficiency than untreated microorganisms, and such treated microorganisms may enhance or facilitate plant growth in contaminated media. What is meant by a mixture "effective to facilitate the growth of plants in contaminated media" is a mixture which increases the growth of plants in contaminated media than without its addition.

The following examples are presented to further illustrate and explain the present invention and should not be taken as limiting in any regard. Unless otherwise indicated, all parts and percentages are by weight, and are based on the weight at the particular stage of the processing being described.

EXAMPLE 1

One form of the inventive composition consists of: a buffered aqueous solution of salts useful to create an isotonic equilibrium so as to avoid creating any drastic osmotic pressure changes within the cells which can damage the cells and adjusted with a solution of about 10% NaOH to a pH of from about 5.5 to about 7.5, and preferably having an adjusted pH of about 6.8–7.2 forming a buffered solution by adding salts known in the art; about 1 gram of inorganic nutrients of nitrogen, phosphorous, and potassium at a ratio of about 15-30-15; between about a $5 \times 10^{-8}$ to about a $5 \times 10^{-3}$ Molar concentration of dibutyryl cAMP, and preferably about $5 \times 10^{-4}$ Molar concentration of dibutyryl cAMP; adding at least one microorganism selected from the group consisting of *Pseudomonas sp., Micrococcus sp., Arthrobacter sp., Candida sp.,* and *Trichoderma sp.,* where the microorganism concentration ranges from about 1,000,000 to about 5,000,000 count of viable cells per 1 liter of aqueous solution, the preferred concentration being 5,000,000 viable cells per 1 liter of aqueous solution; and a concentration of about 1 to about 5 grams of perlite per liter of a solution or slurry of the above ingredients, and preferably a concentration of about 2 grams of perlite is used per liter of a solution or slurry of the above ingredients to form a mixture having the inventive compostion. Salts useful to maintain isotonic equilibrium are Murashige and Skoog salts, and other salts known to those skilled in the art.

EXAMPLE 2

The mixture of Example 1 may be used directly or further processed as in Example 2 below.

After forming the mixture of Example 1, the mixture is then dried at a temperature ranging from about 25° C. to about 55° C., and preferably from about 30° C. to about 50° C., so as to form an anhydrous powder. The drying temperature is preferably maintained within this range in order to ensure that the full biological activity and viability of the final product is achieved.

Alternatively, the mixture may be freeze-dried in a lyophilizer until an anhydrous powder is formed.

EXAMPLE 3

At the time of use, the freeze dried mixture of Example 2 is reconstituted with about 1 liter of seawater to about 1 to about 2 grams of the freeze dried mixture of Example 2 so as to activate the microorganisms and to provide a suspension or slurry. This reconstituted slurry or solution is applied to contaminated media. The same proportion of other aqueous phases, such as fresh water or fresh water with organic and/or inorganic nutrients, may be substituted for the seawater.

EXAMPLE 4

The mixture formed in Example 3 above is applied to contaminated media by spraying, pouring, injecting and/or admixing the inventive compositions with the contaminated media. The compositions are applied to the soil, air, water or plants contaminated with the contaminants. Enough of the mixture is used so as to saturate the soil without resulting in standing, pooling or run-off of the suspension formed by the mixture and the contaminated media. From about 1 liter of mixture per cubic meter of water should be used where the contaminated media is water, such as a river, estuary or aquifer.

EXAMPLE 5

About 1 gram of a sand exposed to natural and seasonal climatic conditions for approximately 10 years is placed in one-dram glass vials. This sand is estimated to contain about a 1,000,000 count of indigenous microorganisms per about 1 gram of soil using fluorescence microscopy. The sand is also tested for the natural concentrations of carbon, hydrogen, and nitrogen by thermo gravimetric analysis. The sand contains approximately 0.09 percent carbon, 0.05 percent hydrogen, and 0.03 percent nitrogen.

About $8 \times 10^{-4}$ millimoles of carbon-13 isotope labeled benzene ($^{13}C_6H_6$) is added to each vial of soil in about 0.2 cc of the aqueous suspension of Example 3 using sodium salt dibutyryl cAMP and USP distilled water and is mixed into the soil vials (hereafter "treated microorganisms"). Biodegradation and Kinetics Data for the treated microorganisms with these prepared vials are taken as described below and listed in Table 4.

A control is made by adding the same amount of carbon-13 isotope labeled benzene to the same amount of soil containing microorganisms as described above, and not containing any dibutyryl cAMP (hereinafter "untreated microorganisms"). An additional control is made by mixing the same amount of dibutyryl cAMP with the same amount of soil containing the indigenous microorganisms as discussed above (hereinafter the "cAMP control group"). Another control is made by mixing about 0.2 cc of water with the same amount of soil as described above (hereinafter the "water control"). Another control is prepared using the same amounts of cAMP, benzene and soil as described above, the soil being sterilized so as to eliminate the biological activity of the microorganisms contained therein (hereinafter the "sterilized control").

Sixty vials (triplicate samples per analysis) containing equal amounts of the treated microorganisms and sixty vials (triplicate samples per analysis) containing equal amounts of the untreated microorganisms are prepared. Twenty vials (single sample per analysis) of each of the controls are prepared. All vials are crimp sealed. A headspace gas sample is withdrawn from each vial, with a 10 microliter gas tight glass syringe, and analyzed over a period of approximately 30 days for amount of carbon-13 isotope carbon dioxide ($^{13}CO_2$), $^{13}C_6H_6$ and oxygen, respectively, by gas chromatography mass spectrometry under selected ion monitoring (SIM) using naturally occurring and stable concentrations of argon as the internal standard. Calibration curves for $^{13}CO_2$ are produced by injecting known amounts of $^{13}CO_2$ gas into the gas chromatograph/mass spectrometer using a gas tight syringe. Peak $^{13}CO_2$ areas measured are ratioed to argon as the internal standard and are plotted to produce a response factor. The response factor is then used to calculate $^{13}CO_2$ concentrations produced in the test.

The data is then analyzed for kinetics and biodegradation efficacy and is provided in Tables 2, 3, 4 and 5 below. The treated microorganisms oxidized and mineralized the $^{13}C_6H_6$ at a significantly faster rate than the untreated microorganisms, the water control and the cAMP control. This is indicated by the First Order Rate Constant for the treated microorganism sample being nearly twice that for the untreated microorganism. The sterilized control exhibits efficacy comparable to the water control, as both are negative for carbon-13 isotope carbon dioxide which is only detected at background levels.

In addition, the oxidation and mineralization of the $^{13}C_6H_6$ in the treated samples is complete in less than thirty days, whereas oxidation and mineralization of the $^{13}C_6H_6$ in the untreated samples is not complete in thirty days. What is meant by "complete" in this context is that there is no detectable amount of $^{13}C_6H_6$ remaining.

The concentration of $^{13}CO_2$ provided in Tables 4 and 5 correlates with biodegradation of the benzene in the samples. The treated samples show a significantly faster rate of biodegradation, as also shown by comparing the VMAX for the treated and untreated microorganisms.

The cAMP control also produced significantly more $^{13}CO2$ than the water control. It is known that approximately one percent of all the carbon on the earth is of the stable carbon-13 isotope type. Therefore, this result supports that the cAMP induced the indigenous microorganisms to further oxidize and mineralize the weathered and previously biodegraded recalcitrant organic matter naturally present in the test soil.

These unexpected results indicate that the cAMP treated microorganisms posses enhanced bioremediating efficacy, thereby facilitating bioremediation and detoxication of the contaminant benzene in the contaminated soil media.

TABLE 2

First Order Rate Constant Data for Treated Microorganisms

| Time, days | Ln C/Co | C |
|---|---|---|
| 3 | −0.80 | 0.38 |
| 7 | −0.81 | 0.37 |
| 11 | −0.83 | 0.37 |
| 13 | −1.91 | 0.12 |
| 16 | −6.40 | 0.00 |
| K = −0.35 | | |

TABLE 3

First Order Rate Constant with the Untreated Microorganisms

| Time, days | Ln C/Co | C |
|---|---|---|
| 3 | −0.80 | 0.38 |
| 7 | −0.80 | 0.38 |
| 11 | −0.80 | 0.38 |
| 13 | −1.34 | 0.22 |
| 16 | −3.16 | 0.04 |
| 19 | −3.43 | 0.03 |
| K = −0.18 | | |

Where;

C=concentration of carbon-13 isotope labeled benzene in micromoles.

Co=concentration of carbon-13 isotope labeled benzene in micromoles at day=0, or 0.842 micromoles.

K=the slope of Ln (C/Co) vs. time, derived by regression analysis as provided in: M. M. Morel and J. G. Hering, *Principles and Applications of Aquatic Chemistry*, Chapt. 3, pp. 103–107 (1993), incorporated herein by reference).

TABLE 4

Biodegradation and Kinetics Data for Treated Microorganisms

| t | $^{13}CO_2$ | f | S | r | r/S |
|---|---|---|---|---|---|
| 3 | 0.01 | 0.01 | 0.38 | 0.002 | 0.005 |
| 7 | 0.04 | 0.02 | 0.37 | 0.002 | 0.006 |
| 11 | 0.08 | 0.04 | 0.37 | 0.003 | 0.009 |
| 13 | 1.53 | 0.67 | 0.12 | 0.052 | 0.419 |
| 16 | 2.27 | 1.00 | 0.00 | 0.062 | |

Eadie-Hofstee Kinetic Constants
Km = 0.12 micromoles
VMAX = 1.66 × 10$^{-3}$ micromoles/day

TABLE 5

Biodegradation and Kinetics Data for Untreated Microorganisms

| t | $^{13}CO_2$ | f | S | r | r/S |
|---|---|---|---|---|---|
| 3 | 0.01 | 0.00 | 0.38 | 0.001 | 0.002 |
| 7 | 0.01 | 0.00 | 0.38 | 0.001 | 0.002 |
| 11 | 0.01 | 0.00 | 0.38 | 0.001 | 0.001 |
| 13 | 0.96 | 0.42 | 0.22 | 0.033 | 0.149 |
| 16 | 2.06 | 0.91 | 0.04 | 0.057 | 1.596 |
| 19 | 2.11 | 0.93 | 0.03 | 0.049 | 1.798 |

Eadie-Hofstee Kinetic Constants
Km = 0.22 micromoles (calculated as in M. Alexander, Biodegradation and Bioremediation (1994), incorporated herein by reference).
VMAX = 2.64 × 10$^{-4}$ micromoles/day (calculated as in K. Valsarj, Elements of Environmental Engineering: Thermodynamics and Kinetics (1995), incorporated herein by reference).
Where,
t = incubation time in days;
$^{13}CO_2$ = concentration of $^{13}CO_2$ in micromoles;
f = fraction of $^{13}C_6H_6$ degraded;
S = micromoles of $^{13}C_6H_6$ remaining
r = f/t or the rate of $^{13}C_6H_6$ degraded
Km = substrate affinity constant; and
VMAX = maximal biodegradation rate in micromoles/day.

When r is plotted versus r/S, the slope is Km and the intercept is VMAX. The lower the value of Km, the greater the microorganism affinity for the substrate—in this case the xenobiotic substrate benzene (i.e., $^{13}C_6H_6$). Thus, the higher the VMAX the faster the biodegradation which is a measure enzyme velocity associated with the biodegradation of the contaminant.

EXAMPLE 6

One test group and three control groups consisting of twenty pots per group to which a 4 ounce (oz.) homogeneous soil mixture (1 part top soil, 1 part sand, 1 part pro-mix) is added.

The Diesel, Microbe and dibutyryl cAMP contaminant test group (DM+cAMP), receives 10 cc buffered aqueous solution containing Murashige & Skoog Salt Mixture pH adjusted to 5.7 with 1N NaOH and microorganisms (about 5,000,000 microbes per 5 grams perlite per liter of USP distilled water) treated with 5×10$^{-4}$ Molar concentration of dibutyryl cAMP and 2 cc of diesel fuel contaminant.

The non-contaminant Control group (C) receives 10 cc buffered aqueous solution containing Murashige & Skoog Salt Mixture pH adjusted to 5.7 with 1N NaOH.

The Diesel contaminant control group (D) receives 10 cc buffered aqueous solution containing Murashige & Skoog Salt Mixture pH adjusted to 5.7 with 1N NaOH and 2 cc of diesel fuel contaminant.

The Diesel and Microbe contaminant control group (DM) receives 10 cc buffered aqueous solution containing Murashige & Skoog Salt Mixture pH adjusted to 5.7 with 1N NaOH and microorganisms (about 5,000,000 per 5 grams perlite per liter of USP distilled water) and 2 cc of diesel fuel contaminant.

All control groups, including the test group containing the soil, microorganisms and cAMP derivative are fertilized with about 20 cc of a 15-30-15 solution of inorganic nutrients of nitrogen, phosphorous, and potassium.

Three radish seeds are planted in the pots and grown in a greenhouse environment. Shortly after germination each pot is thinned to one plant per pot to minimize seedling growth variation. The pots are watered on a regular basis and then the entire plants (above and below ground growth) are harvested after a period of time that indicates mature growth. Each plant's dry biomass (weight in grams) is measured and compared with a control group consisting of amounts of soil and radish seeds prepared and grown as described above that received no diesel fuel, no microorganisms and no dibutyryl cAMP. The radishes grown in the mixture of dibutyryl cAMP, microorganisms, diesel fuel, and soil exhibited no significant difference in biomass between the control group. Table 6 and Table 7 show these results. In Table 7, the first column represents the mean difference between the groups compared. The second column reports the mean difference required to be significant at a 5% level. The third column reports the probability that the difference between the group is significant, that is if the reported P-value is less than a pre-specified significance level. The results show that the presence of the contaminant diesel fuel had a significant negative effect on the plant growth and total biomass dry weight of the radish plants, yet there was no statistically significant difference between the control and radish plants with the contaminant diesel fuel and the treated microorganisms.

TABLE 6

Mean Biomass Weight-Dry Weight Basis

| Group Identification | Number of Radish Plants | Mean Weight |
|---|---|---|
| Control = C | 15 Count | 0.6 grams |
| Diesel = D | 18 Count | 0.4 grams |
| Diesel & Microbes = DM | 18 Count | 0.3 grams |
| Diesel, cAMP & Microbes = [DM + cAMP] | 18 Count | 0.6 grams |

TABLE 7

Fisher's PLSD for Total Biomass
Dry Weight Basis (5% Significance Level)

| Groups Compared | Mean Difference | Critical Difference | P-Value | Significance |
|---|---|---|---|---|
| C, D | 0.150 | 0.135 | 0.0306 | Positive |
| C, DM | 0.239 | 0.135 | 0.0007 | Positive |
| C, DM + cAMP | 0.016 | 0.135 | 0.8100 | Negative |

PLSD = Probability Least Squares Differences.
C = Represents the Control group of radish plants in soil with no dibutyryl cAMP, no microorganisms, and no diesel fuel.
D = Represents radish plants in soil with diesel fuel.
DM = Represents radish plants in soil with diesel fuel and untreated microbes (not treated with dibutyryl cAMP).
(DM + cAMP) = Represents radish plants in soil with diesel fuel and microbes treated with dibutyryl cAMP.

Another application of the present invention can include employing the use of cAMP treated nitrogen fixing microorganisms, such as *Rhizobium meliloti* (Rhizobium sp. soil bacteria) in an amount effective to facilitate bioremediation and/or detoxication of contaminants in a contaminated soil media and/or facilitating the growth of agricultural products such as soybeans, peanuts, and other crops that utilize nitrogen fixing bacteria such as Rhizobium sp. grown in uncontaminated media. Nitrogen fixing microorganisms treated with cAMP may induce enhanced nitrogen fixation when used either alone in a soil medium or in a plant microorganism symbiosis. The inventive composition and method can also contain microorganisms which produce adenylyl cyclase, by way of example and not as a limitation to the present invention, in Rhizobium sp. soil bacteria, including microorganisms produced using recombinant DNA technology.

Although the invention has been described with reference to particular ingredients and formulations and the like, these are not intended to exhaust all possible arrangements or features, and indeed many other modifications and variations will be ascertainable to those of skill in the art. It is intended that all such reasonable modifications and variations be included within the scope of the invention, which is defined by the following claims.

What is claimed is:

1. A composition to facilitate bioremediation of contaminants in contaminated media comprising: a mixture of at least one compound selected from the group consisting of cAMP, cGMP, forskolin, adenylate cyclase, guanylate cyclase, a derivative of cAMP, a derivative of cGMP, a derivative of forskolin, a derivative of adenylate cyclase, a derivative guanylate cyclase, a homolog of cAMP, a homolog of cGMP, a homolog of forskolin, a homolog of adenylate cyclase, a homolog of guanylate cyclase, an analog of cAMP, an analog of cGMP, an analog of forskolin, an analog of adenylate cyclase and an analog of guanylate cyclase; and at least one microorganism specie; wherein said mixture is effective to facilitate bioremediation of the contaminants in the contaminated media.

2. The composition of claim 1 wherein said mixture exhibits increased enzyme velocity as measured by VMAX when applied to the contaminated media compared to the contaminated media without said mixture.

3. The composition of claim 1 wherein said mixture exhibits decreased xenobiotic substrate affinity as measured by Km when applied to the contaminated media compared to the contaminated media without said mixture.

4. The composition of claim 1 wherein said compound is a derivative of cAMP selected from the group consisting of salts of $N^6$-monacetyladenosine 3':5'-cyclic monophosphate, $N^6$-monobutyryladenosine 3':5'-cyclic monophosphate, $N^6$-monooctanoyladenosine 3':5'-cyclic monophosphate, 2'-O-monobutyryladenosine 3':5'-cyclic monophosphate, $N^6$-2'-O-diacetyladenosine 3':5'-cyclic monophosphate, and $N^6$,2'-O-dibutyryladenosine 3':5'-cyclic monophosphate.

5. The composition of claim 1 further comprising theophylline.

6. The composition of claim 4 wherein said microorganism specie is selected from the group consisting of *Pseudomonas, Micrococcus, Arthrobacter, Candida, Phanerochate chrysosporium; Phanerochate;* and *Trichoderma.*

7. A composition to facilitate the growth of plants grown in contaminated media comprising: a mixture of at least one compound selected from the group consisting of cAMP, cGMP, forskolin, adenylate cyclase, guanylate cyclase, a derivative of cAMP, a derivative of cGMP, a derivative of forskolin, a derivative of adenylate cyclase, a derivative guanylate cyclase, a homolog of cAMP, a homolog of cGMP, a homolog of forskolin, a homolog of adenylate cyclase, a homolog of guanylate cyclase, an analog of cAMP, an analog of cGMP, an analog of forskolin, an analog of adenylate cyclase and an analog of guanylate cyclase; and at least one microorganism specie; said mixture effective to facilitate the growth of plants grown in the contaminated media.

8. The composition of claim 7 wherein said compound is a derivative of cAMP selected from the group consisting of salts of $N^6$-monacetyladenosine 3':5'-cyclic monophosphate, $N^6$-monobutyryladenosine 3':5'-cyclic monophosphate, $N^{6'}$-monooctanoyladenosine 3':5'-cyclic monophosphate, 2'-O-monobutyryladenosine 3':5'-cyclic monophosphate, $N^6$-2'-O-diacetyladenosine 3':5'-cyclic monophosphate, and $N^6$,2'-O-dibutyryladenosine 3':5'-cyclic monophosphate.

9. The composition of claim 8 wherein said mixture is also effective to facilitate the growth of plants using nitrogen fixing bacteria grown in uncontaminated media.

10. The composition of claim 9 wherein at least one of said microorganism specie comprises Rhizobium sp.

11. A method to facilitate bioremediation of contaminants in contaminated media, comprising the steps of:
providing a mixture of at least one compound selected from the group consisting of cAMP, cGMP, forskolin, adenylate cyclase, guanylate cyclase, a derivative of cAMP, a derivative of cGMP, a derivative of forskolin, a derivative of adenylate cyclase, a derivative guanylate cyclase, a homolog of cAMP, a homolog of cGMP, a homolog of forskolin, a homolog of adenylate cyclase, a homolog of guanylate cyclase, an analog of cAMP, an analog of cGMP, an analog of forskolin, an analog of adenylate cyclase and an analog of guanylate cyclase; and at least one microorganism specie to form a mixture, wherein said mixture has bioremediation activity; and
applying said mixture to the contaminated media in an amount effective to facilitate bioremediation of the contaminants.

12. The method of claim 11 wherein said compound is a derivative of cAMP selected from the group consisting of salts of $N^6$-monacetyladenosine 3':5'-cyclic monophosphate, $N^6$-monobutyryladenosine 3':5'-cyclic monophosphate, $N^6$-monooctanoyladenosine 3':5'-cyclic monophosphate, 2'-O-monobutyryladenosine 3':5'-cyclic monophosphate, $N^6$-2'-O-diacetyladenosine 3':5'-cyclic monophosphate, and $N^{6'}$,2'-O-dibutyryladenosine 3':5'-cyclic monophosphate.

13. The method of claim 12 further comprising the step of injecting the contaminated media and said mixture with gaseous oxygen or air.

14. The method of claim 12 further comprising the step of injecting the contaminated media and said mixture with a second compound to elevate the dissolved oxygen concentration in said contaminated media.

15. A method to make a composition to facilitate bioremediation of contaminants in contaminated media, comprising the steps of:
providing at least one compound selected from the group consisting of cAMP, cGMP, forskolin, adenylate cyclase, guanylate cyclase, a derivative of cAMP, a derivative of cGMP, a derivative of forskolin, a derivative of adenylate cyclase, a derivative guanylate cyclase, a homolog of cAMP, a homolog of cGMP, a homolog of forskolin, a homolog of adenylate cyclase, a homolog of guanylate cyclase, an analog of cAMP, an analog of cGMP, an analog of forskolin, an analog of adenylate cyclase and an analog of guanylate cyclase in a solution to form an aqueous phase; and
adding at least one microorganism specie to said aqueous phase to form a mixture, wherein said mixture is effective to facilitate bioremdiation of the contaminants.

16. The method of claim 15 further comprising the step of adding salts to maintain isotonic equilibrium of said aqueous phase.

17. The method of claim 15 further comprising the step of drying said mixture to form an anhydrous powder.

18. The method of claim 17 further comprising the step of mixing an inert adsorbent selected from the group consisting of kaolin, vermiculite, perlite, zeolites, glass beads and clay with said mixture.

19. The method of claim 17 further comprising the step of reconstituting said anhydrous powder to an aqueous phase wherein said aqueous phase is effective to facilitate bioremdiation of the contaminants.

20. A composition to facilitate detoxication of contaminants in contaminated media comprising: a mixture of at least one compound selected from the group consisting of cAMP, cGMP, forskolin, adenylate cyclase, guanylate cyclase, a derivative of cAMP, a derivative of cGMP, a derivative of forskolin, a derivative of adenylate cyclase, a derivative guanylate cyclase, a homolog of cAMP, an analog of cGMP, a homolog of forskolin, a homolog of adenylate cyclase, a homolog of guanylate cyclase, an analog of cAMP, an analog of cGMP, an analog of forskolin, an analog of adenylate cyclase and an analog of guanylate cyclase; and at least one microorganism specie; wherein said mixture is effective to facilitate detoxication of the contaminants.

21. A composition to facilitate bioremediation of contaminants in contaminated media comprising:
a mixture of at least one compound selected from the group consisting of cAMP, cGMP, forskolin, adenylate cyclase, guanylate cyclase, a derivative of cAMP, a derivative of CGMP, a derivative of forskolin, a derivative of adenylate cyclase, a derivative guanylate cyclase, a homolog of cAMP, a homolog of CGMP, a homolog of forskolin, a homolog of adenylate cyclase, a homolog of guanylate cyclase, an analog of cAMP, an analog of cGMP, an analog of forskolin, an analog of adenylate cyclase and an analog of guanylate cyclase; and at least one microorganism specie; wherein said mixture is effective to facilitate bioremediation of the contaminants in the contaminated media and wherein said mixture exhibits increased enzyme velocity as measured by VMAX when applied to the contaminated media compared to the contaminated media without said mixture and wherein said mixture exhibits decreased xenobiotic substrate affinity as measured by Km when applied to the contaminated media compared to the contaminated media without said mixture.

22. A composition to facilitate bioremediation of contaminants in contaminated media comprising: p1 a mixture of at least one compound selected from the group consisting of cAMP, cGMP, forskolin, adenylate cyclase, guanylate cyclase, a derivative of cAMP, a derivative of CGMP, a derivative of forskolin, a derivative of adenylate cyclase, a derivative guanylate cyclase, a homolog of cAMP, a homolog of cGMP, a homolog of forskolin, a homolog of adenylate cyclase, a homolog of guanylate cyclase, an analog of cAMP, an analog of cGMP, an analog of forskolin, an analog of adenylate cyclase and an analog of guanylate cyclase;
theophylline; and
at least one microorganism specie; wherein said mixture is effective to faciliate bioremediation of the contaminants in the contaminated media and wherein said mixture exhibits increased enzyme velocity as measured by VMAX when applied to the contaminated media compared to the contaminated media without said mixture.

\* \* \* \* \*